(12) United States Patent
Zheng et al.

(10) Patent No.: US 8,819,877 B2
(45) Date of Patent: Sep. 2, 2014

(54) METHOD AND DEVICE FOR PATIENT LOADING AND POSITIONING

(75) Inventors: Mike Q. Zheng, Columbia, MD (US); Xinsheng Cedric Yu, Clarksville, MD (US); Xiumin Diao, Columbia, MD (US); Bo Zhou, Towson, MD (US)

(73) Assignee: Xcision Medical Systems, LLC, Columbia, MD (US)

( * ) Notice: Subject to any disclaimer, the term of this patent is extended or adjusted under 35 U.S.C. 154(b) by 651 days.

(21) Appl. No.: 13/020,457

(22) Filed: Feb. 3, 2011

(65) Prior Publication Data

US 2012/0198624 A1 Aug. 9, 2012

(51) Int. Cl.
*A61B 6/04* (2006.01)
*A61G 13/04* (2006.01)

(52) U.S. Cl.
USPC ............... 5/601; 5/943; 5/600; 5/607; 5/611

(58) Field of Classification Search
USPC .............. 5/600, 601, 607, 608, 610, 616, 943
See application file for complete search history.

(56) References Cited

U.S. PATENT DOCUMENTS

| | | | | |
|---|---|---|---|---|
| 1,925,425 A | | 9/1933 | Wilent | |
| 2,222,888 A | * | 11/1940 | Haupt | 5/601 |
| 2,680,046 A | * | 6/1954 | Stava | 5/601 |
| 2,693,399 A | * | 11/1954 | Vaughn | 5/601 |
| 2,840,429 A | * | 6/1958 | McDonald | 5/610 |
| 2,854,302 A | * | 9/1958 | Haupt | 5/601 |
| 2,913,738 A | * | 11/1959 | Wise | 5/616 |
| 3,149,229 A | * | 9/1964 | Morel | 5/601 |
| 4,015,836 A | | 4/1977 | Redington et al. | |
| 4,603,845 A | * | 8/1986 | Schmedemann | 5/610 |
| 5,983,424 A | | 11/1999 | Näslund | |
| 7,895,688 B1 | * | 3/2011 | Rowes et al. | 5/612 |
| 2006/0259267 A1 | * | 11/2006 | Narayanasamy | 702/150 |
| 2007/0238949 A1 | * | 10/2007 | Wang et al. | 600/407 |

FOREIGN PATENT DOCUMENTS

| | | |
|---|---|---|
| WO | 9742876 | 11/1997 |
| WO | 2005099578 | 10/2005 |

* cited by examiner

*Primary Examiner* — William Kelleher
*Assistant Examiner* — David R Hare
(74) *Attorney, Agent, or Firm* — Ober, Kaler, Grimes & Shriver; Royal W. Craig (57) ABSTRACT

A method and device for accurately positioning patients for imaging and radiotherapy is disclosed. The device includes a support platform (such as a bed, a table, a couch, a chair, etc.) connected to a fixed base by at least two and preferably four offset supporting arms. The support arms are journaled into the support platform at passive-rotatable pivot joints and are journaled into the base at active-rotatable pivot points. The base contains actuators (manual or powered by motors, pneumatics or hydraulics) for articulating the support arms. The relative lengths of the support arms may be varied to create a pre-defined trajectory of the support platform, between a starting spatial position and orientation to an ending spatial position and orientation, and through a continuous range there between. This makes it possible to position a patient within a range from a low, standing up position to a high, forwarding, prone or supine position, or vice versa.

29 Claims, 8 Drawing Sheets

METHOD AND DEVICE FOR PATIENT LOADING AND POSITIONING

TECHNICAL FIELD

The present invention generally relates to radiotherapy equipment and, more particularly, to a method and device for spatially positioning patients for imaging and radiation treatments.

BACKGROUND

There are various imaging techniques used for detection of physical illnesses and abnormalities, as well as for determining the stage of an illness (e.g., how advanced a cancer is), and for precisely mapping the body to aid in directing surgery, radiographic treatments, and other treatments. Such imaging techniques include X-Ray Imaging, CT Scans, Nuclear Imaging (PET and SPECT), Ultrasound, Magnetic Resonance Imaging (MRI), Digital Mammography, Virtual Colonoscopy, Sentinel Node Mapping for Breast Cancer Staging, Image-Guided Brain Surgery, and others. The various techniques all require some degree of patient positioning, though the positioning for the various techniques may be quite different. Moreover, some techniques require frequent patient repositioning with a very high degree of accuracy.

For example, during the present inventor's recent study of Stereotactic Body Radiation Therapy (SBRT) of breast cancer, patients equipped with breast immobilizing devices and other imaging electronics had to be transferred from an upright position to a prone position very precisely before initiating the imaging and radiation treatments, and then back from prone to upright immediately afterwards.

It can be a challenging task for healthcare staff to change a patient's position from one orientation to another, such as from upright to prone and vice versa. There are a number of prior art efforts to improve patient transposition and positioning for medical procedures.

For example, Harwood et al (WO 97142876) proposed a multiple joint patient table to alter patient's spatial orientation. Redington, at al (U.S. Pat. No. 4,015,836) and Wilent (U.S. Pat. No. 1,925,425) both suggest patient positioning tables rotatable over a single pivot to achieve different orientations. Naslund (U.S. Pat. No. 5,983,424 and W02041020819) invented a patient table-tilting device using a belt transporting mechanism. Also, Saracen at al (W0120051099578) used a robotic structure for patient positioning. Although each of these prior art attempts resolved certain specific issues, there is still a need for a simpler and more versatile and precisely controllable patient loading/positioning device or method for use across a variety of different imaging and/or therapeutic procedures.

The prior art efforts do not provide a trajectory-adjustable method or device for patient positioning procedure, nor a combination of translation and rotation needed for certain applications, such as to transfer a patient from an upright standing position to a forwarding prone lying position and vice versa. Accordingly, an object of the invention is to provide a solution for these much needed features.

SUMMARY OF THE DISCLOSURE

It is the primary objective of the present disclosure to provide a method and device to allow easy and accurate patient positioning for imaging and treatment using Computed Tomography (CT), MRI and radiation therapy. It is another objective of the present invention to provide a method and device as described above which can significantly change the patient's starting position/orientation, ending position/orientation, and the trajectories in between by changing its mechanical configurations dynamically or preset for each patient positioning procedure.

The above objects are achieved in accordance with the present invention by a method of positioning and novel patient positioning device in which a support platform (such as a bed, a table, a couch, a chair, etc.) is spatially-articulated by at least two and preferably four offset supporting arms. The support arms are journaled into both ends of the support platform at passive-rotatable pivot points and extend to a rigid base. The support arms are journaled into the base at offset active-rotatable pivot points, and the base contains actuators (manual or powered by motors, pneumatics or hydraulics) for articulating the support arms. The powered actuators are electronically-controlled by, and provide positional feedback to a programmable controller for more precise positioning and for pre-programmed positioning capability. In a preferred embodiment there are two pairs of articulated support arms each providing quadrilateral support to the support platform. Given the basic mechanical configuration of the system the relative lengths of the two arm of each pair may be varied to create a pre-defined trajectory of the support platform, between a starting spatial position and orientation to an ending spatial position and orientation, and through a continuous range there between. This makes it possible to position a patient within a range from a low, standing up position to a high, forwarding, prone or supine position, or vice versa. The basic mechanical configuration of the system can be changed dynamically, either through actuators or manually, to allow a broad range of starting position/orientation, ending position/orientation, and trajectories in between to meet spatial and clinical requirement.

BRIEF DESCRIPTION OF THE FIGURES

Reference will now be made in detail to the preferred embodiments of the present invention, examples of which are illustrated in the accompanying drawings. Wherever possible, the same reference numbers will be used throughout the drawings to refer to the same or like parts, and the same or like parts visible in a left-side view are designated with an "a" suffix while those in a right-side view are designated with an "b" suffix.

FIG. 2(A-B) are left-side illustrations showing the operation of the above-described device 1 between a starting spatial position and orientation and an ending spatial position and orientation.

DETAILED DESCRIPTION

The present disclosure is a patient positioning method and device which is particularly suited for imaging and radiation treatments. Using the disclosed method and device, one can adjust both the spatial position and orientation of a patient in either a prone or supine position easily and accurately.

Figure 1:
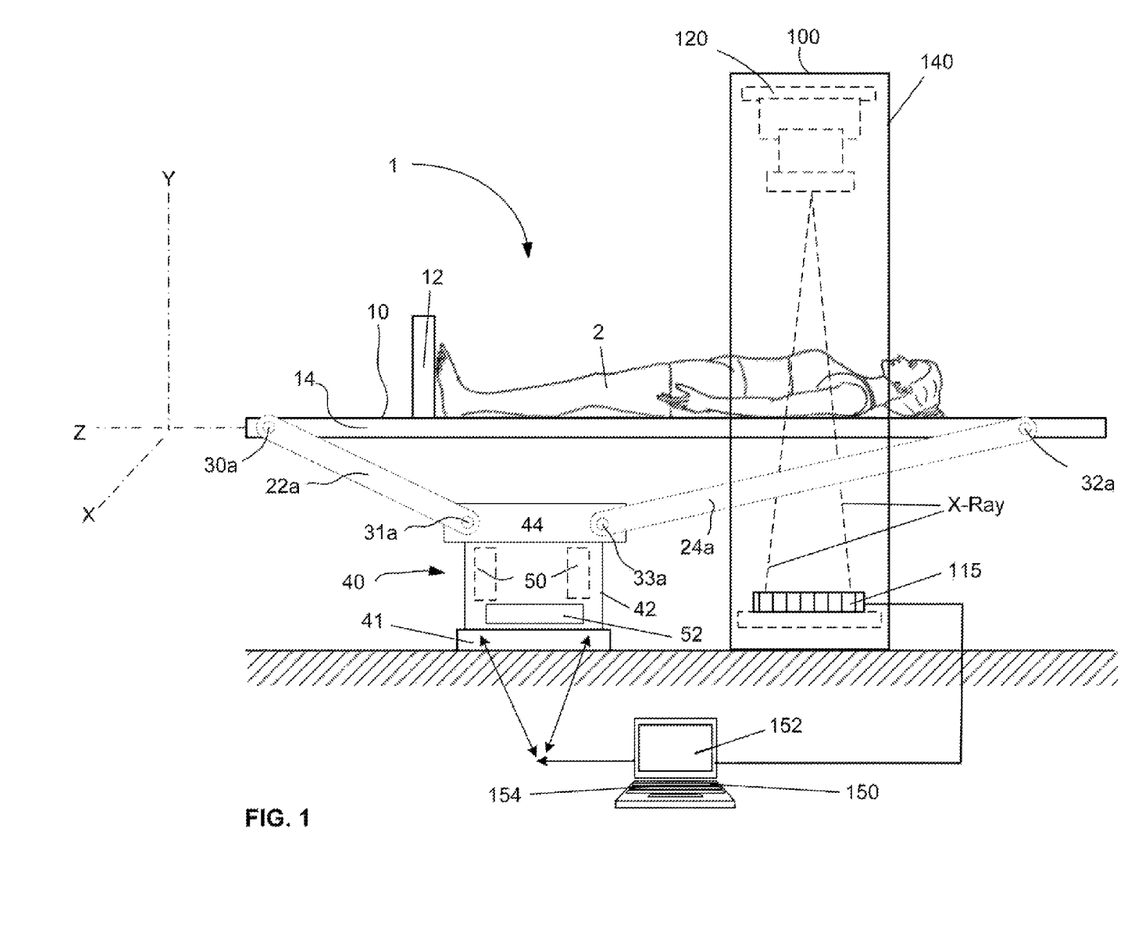
FIG. 1 is a left-side illustration of a patient positioned on the disclosed imaging/treatment patient positioning device 1 of the present invention.

Referring to FIG. 1, the patient 2 is positioned on a support platform 10 which may be a table (as shown) or bed, couch, chair, etc. The support platform 10 comprises a primary torso support section 14 and a foot support 12 perpendicularly attached to the torso support section 14, both preferably sufficient to support the entire weight of the patient. The position of foot support 12 may be adjustable lengthwise along the length of support platform 10 to adjust the relative position of the patient thereon. Note that a thin mattress or pad may be interposed between the patient 2 and the top of the torso support section 14 for the patient's comfort. Different materials can be used for the torso support section 14 and a foot support 12, though for MRI imaging, the materials used for torso support section 14 should be non-ferromagnetic so that the support platform 10 will not distort the magnetic field in the imaging space.

The support platform 10 is spatially-articulated by at least two offset supporting arms 22a, 24a on one side of the support platform 10, and preferably two pair of offset supporting arms 22a, 22b, 24a, 24b on both sides of the support platform 10, the supporting arms 22a-b and 24a-b of each pair (22b and 24b here being obscured) being identical in length. The lower support arms 22a-b are journaled into the opposing sides of the torso support section 14 to provide bilateral support, such as proximate the bottom-end corners, and the upper support arms 24a-b are journaled into the opposing sides of the torso support section 14 adding quadrilateral support, and these may be proximate the top-end corners. One skilled in the art should understand that the pivot joints in the support platform 10 can be any place, not necessarily near the four corners. All of the supporting arms 22, 24 are pivotally connected to the torso support section 14 at passive-rotatable pivot points 30a, 30b, 32a, 32b, which are preferably sealed spherical roller bearings for long-life performance and reliability, and to promoting a clean working environment. The two pairs of offset support arms 22a, 22b extend to a rigid base 40. The support arms are journaled into the base at offset active-rotatable pivot points 31a, 31b, 33a, 33b, and the base 40 of the illustrated embodiment includes a cabinet 42 seated atop a floor support 41, and a rotating pedestal 44 atop cabinet 42. In the preferred embodiment actuators 50 are coupled to the active-rotatable pivot points 31a, 31b or 33a, 33b, or both pairs to effect articulation of the two pair of offset supporting arms 22a, 22b, 24a, 24b, and the arms may be axled together so that one actuator 50 per pair is necessary. However, one skilled in the art should understand that one or two actuators 50 may be used, inasmuch as a single actuator can drive the bed from any one or more of the eight pivot points in the base 40 or support platform 10. Moreover, if the offset supporting arms 22a, 22b, 24a, 24b are axled together in pairs as per above (axle 31a/31b and 33a/33b), only a single actuator 50 is necessary to drive both axles 31a/31b and 33a/33b. Mechanically, the offset supporting arms 22a, 22b, 24a, 24b can be driven from the pivot joints 30, 32 on the patient support platform 10 as well, using actuator(s) in the bed or external actuators. All such variations are considered to be within the scope and spirit of the present invention. The actuators 50 may be manual, but are preferably powered by motors, pneumatics or hydraulics for articulating the support arms 22, 24. The actuators 50 may be coupled to the support arms 22,24 by offset pinions or gear mechanisms.

When in use, the patient 2 is positioned on a support platform 10 in an existing imaging or treatment system, and FIG. 1 schematically illustrates a X-ray imager 100. The imager 100 has a frame 140 and an X-ray source 120 mounted in the frame 140. Source 120 emits a conical beam that is shaped with collimators (not shown in FIG. 1 but generally known). X-ray radiation emanating from the X-ray source 120 penetrates the patient 2 to be examined and impinges on an X-ray detector 115 located beneath. The X-ray detector 115 generates signals corresponding to the intensity of the incident X-ray radiation and transmits the information to a computer 150 that calculates images of the patient 2. These images can be shown on a monitor 152, and a keyboard 154 is typically provided for user-operation of the computed tomography apparatus 100. In accordance with the present invention, the computer 150 is also in bi-directional network communication with an actuator controller circuit 52 resident in base 42, and hosts a software program for receiving position feedback from actuators 50 and for controlling their positioning accordingly.

Figure 2:
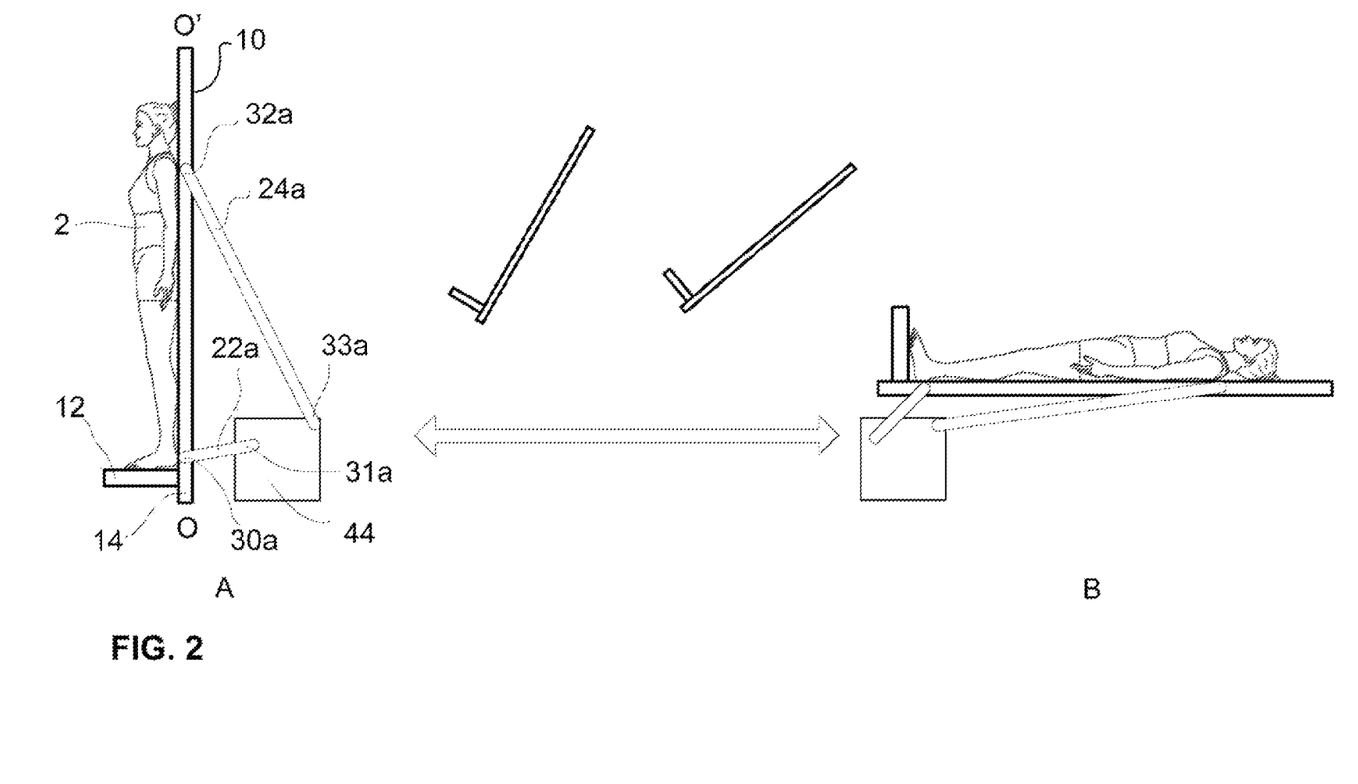

FIG. 2(A-B) illustrates the operation of the above-described device between a starting spatial position and orientation (here a low, standing up position as at (A)) to an ending spatial position and orientation (here a high, forwarding, prone or supine position (B), and through a continuous range there between. Initially, with the torso support section 14 being held in a vertical position and the foot support 12 horizontal, the patient 2 needs only back up against the support platform 10 and step up onto the foot support 12. By computer 150 controlled synchronous actuation of actuators 50 the lower supporting arms 22a, 22b are pivoted resulting in the torso support section 14 being held in a horizontal position and the foot support 12 vertical.

A midpoint of the platform support 10 traverses an ovoid path, and the patient is slowly elevated up the y-axis of FIG. 1) while being rotated rearward about 90 degrees (about the x-axis) and also displaced rearward (along the z-axis) without any force being applied to the passive-rotatable pivot points 30,32. Only the offset active-rotatable pivot points 31, or, 33, or both are powered. The controlled combination of rotation with spatial translation of the support platform 10 makes it possible to position a patient within a range from low, standing to a high, forwarding, prone or supine position, and vice versa. Moreover, this is much easier for the patient 2 and the attending since the patient can embark while standing upright, and the trajectory of the support platform 10 eases them back and into the CT scanner 100 to the position shown in FIG. 1, then back out for a standing disembark.

One skilled in the art should readily understand that the two pair of articulated support arms 22a-b and 24a-b of FIG. 1 add stability and reduce torque requirements by each supporting a corner of the support platform 10. However, the very same principle and structural operation can be accomplished with only two articulated support arms 22a, 24a on only one side (either side) of the support platform 10.

Given the basic mechanical configuration of the system described above, it should also be apparent that the relative lengths of the two arms 22, 24 of each pair and the offset of the pivot joints 30-33 may be varied to create a pre-defined trajectory of the support platform, between any starting spatial position and orientation to an ending spatial position and orientation, and through a continuous range there between. The trajectory shown in FIG. 2 comprises a first spatial position offset to the left side of the base 40 and a vertical orientation, and this is translated into a second spatial position offset to the right of the base 40 and a horizontal orientation. This trajectory is well-suited for easy-loading of a patient into most conventional imaging or treatment systems in a lying prone or supine position. The trajectory is achieved by a pair of lower support arms 22a, 22b that are approximately one third the length of the pair of upper support arms 24a, 24b.

Figure 3:
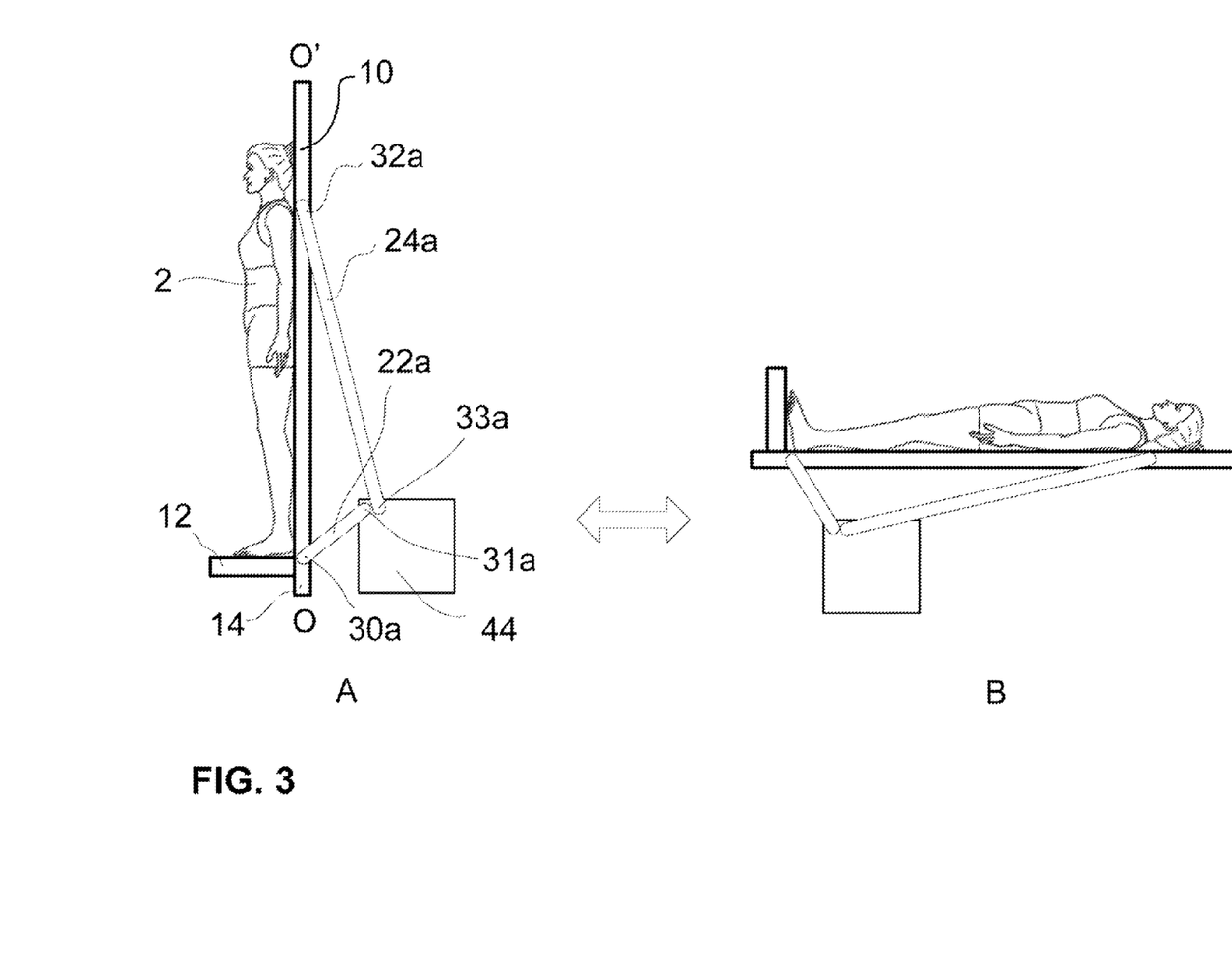
FIG. 3 is a left-side schematic illustration of another embodiment in which the relative lengths of the arms 22, 24, the locations of the joints in the patient support platform 10 (30, 32), and the joints in the base cabinet 44 (31, 33) are arranged to achieve a reduced translational shift forward to the horizontal final position (less forwarding).

FIG. 3 (A-B) is a schematic illustration of another embodiment in which the relative lengths of the lower arm(s) 22 are increased to about one-half the length of the upper arm(s) 24, and the offset distance between the lower pivot joints 31a, 33a is reduced, these two changes combining to establish the same trajectory shown in FIG. 2 (first spatial position offset to the left side of the base 40 and a vertical orientation to second spatial position offset to the right of the base 40 and a horizontal orientation), but compacted into a greatly reduced horizontal translation along the z-axis of FIG. 1.

Figure 4:
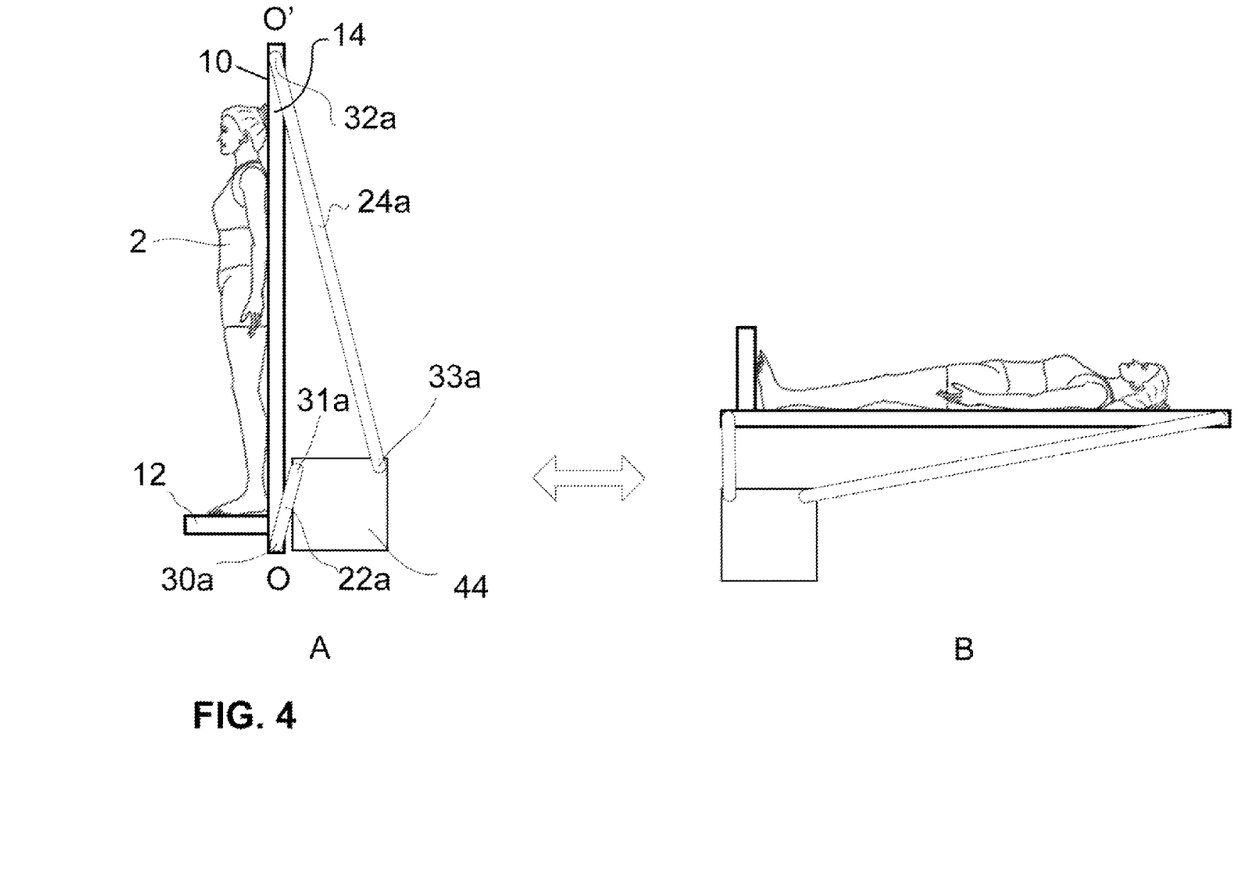
FIG. 4 is a schematic illustration of another embodiment in which the relative lengths of the arms 22, 24, the locations in the patient support platform 10 (30, 32) and in the base cabinet 44 (31, 33) are arranged to achieve increased translational shift forward to the horizontal final position(more forwarding).

FIG. 4 (A-B) is a schematic illustration of another embodiment in which the relative lengths of the lower arm(s) 22 are decreased to about one-quarter the length of the upper arm(s) 24, and the offset distance between the lower pivot joints 32a, 32b is increased, these two changes combining to establish the same trajectory shown in FIGS. 2-3 (first spatial position offset to the left side of the base 40 and a vertical orientation to second spatial position offset to the right of the base 40 and a horizontal orientation), but within a greatly increased horizontal translation along the z-axis of FIG. 1.

Figure 5:
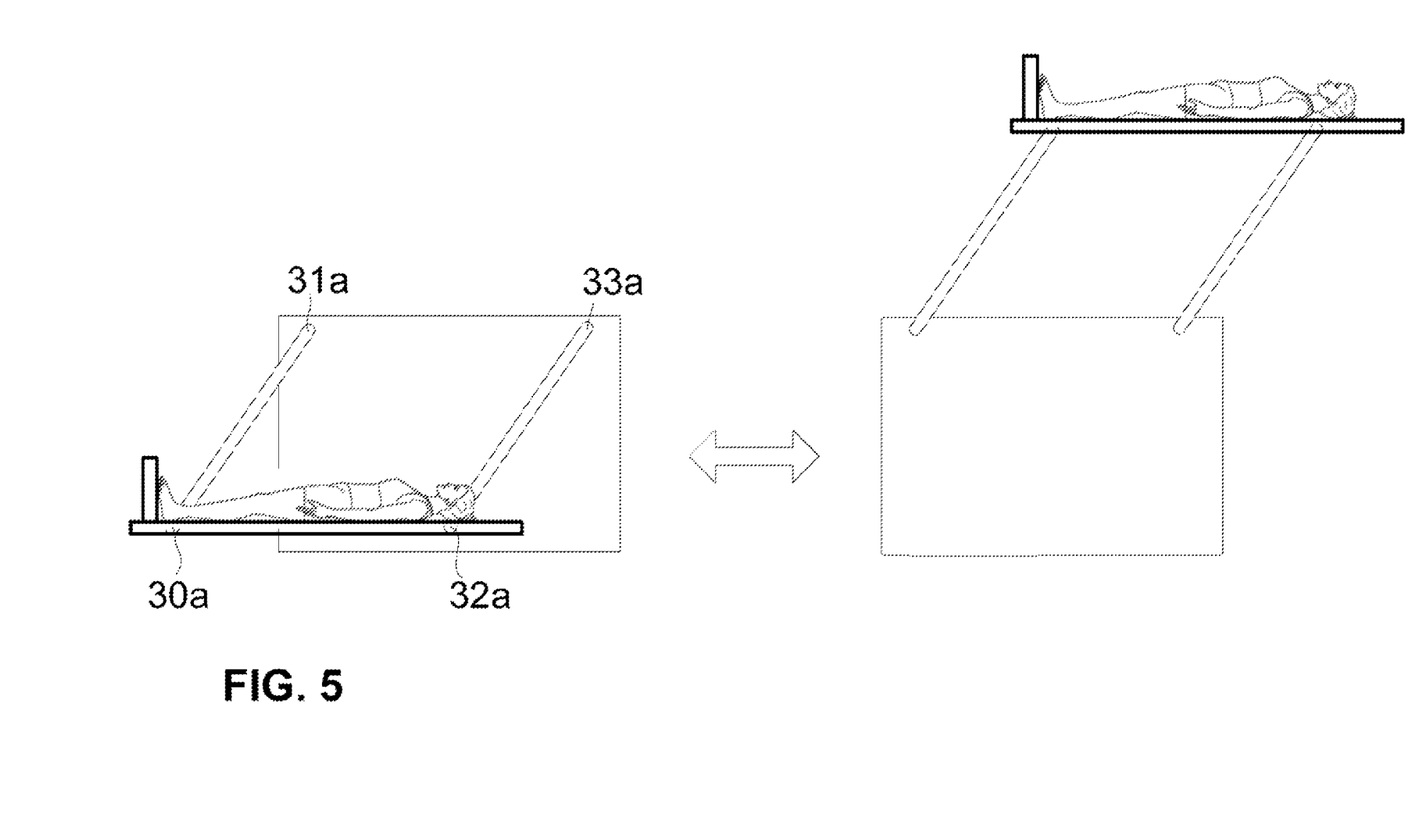
FIG. 5 is a schematic illustration of another embodiment in which the relative lengths of the lower arm(s) 22 are equal to the upper arm(s) 24 so the patient's spatial position and/or elevation is changed while remaining the original (here horizontal) orientation.

FIG. 5 is a schematic illustration of another embodiment in which the relative lengths of the lower arm(s) 22 are equal to the length of the upper arm(s) 24, and the offset distance between the lower pivot joints 31a, 33a is increased. These two changes combine to establish a simple circular trajectory in which the first spatial position is horizontal and offset to the left side of the base 40 at a low elevation, and a second spatial position offset to the right of the base 40 at a higher elevation (still at a horizontal orientation). The orientation of the patient does not change but they are translated within the y-z axis of FIG. 1.

By varying the length of the upper versus lower support arms 22, 24 and the offset of the pivot joints 30-33 the trajectory may be controlled between any starting spatial position and orientation to an ending spatial position and orientation, and through a continuous range there between. The amount of forward translational motion can also be controlled/adjusted by varying the location of the pivot joints 31 and 33 along the length of the support platform 10.

It should now be apparent that the above-described device allows easy and accurate patient setup for imaging or radiographic treatment, including easy movement and stabilization of a patient. The device is capable of patient repositioning from one spatial body position and orientation to another, keeping constant the plane of the patient's body or, if needed, rotational movement at any point in order to alter both spatial position and body orientation within an x-y plane.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

Figure 6:
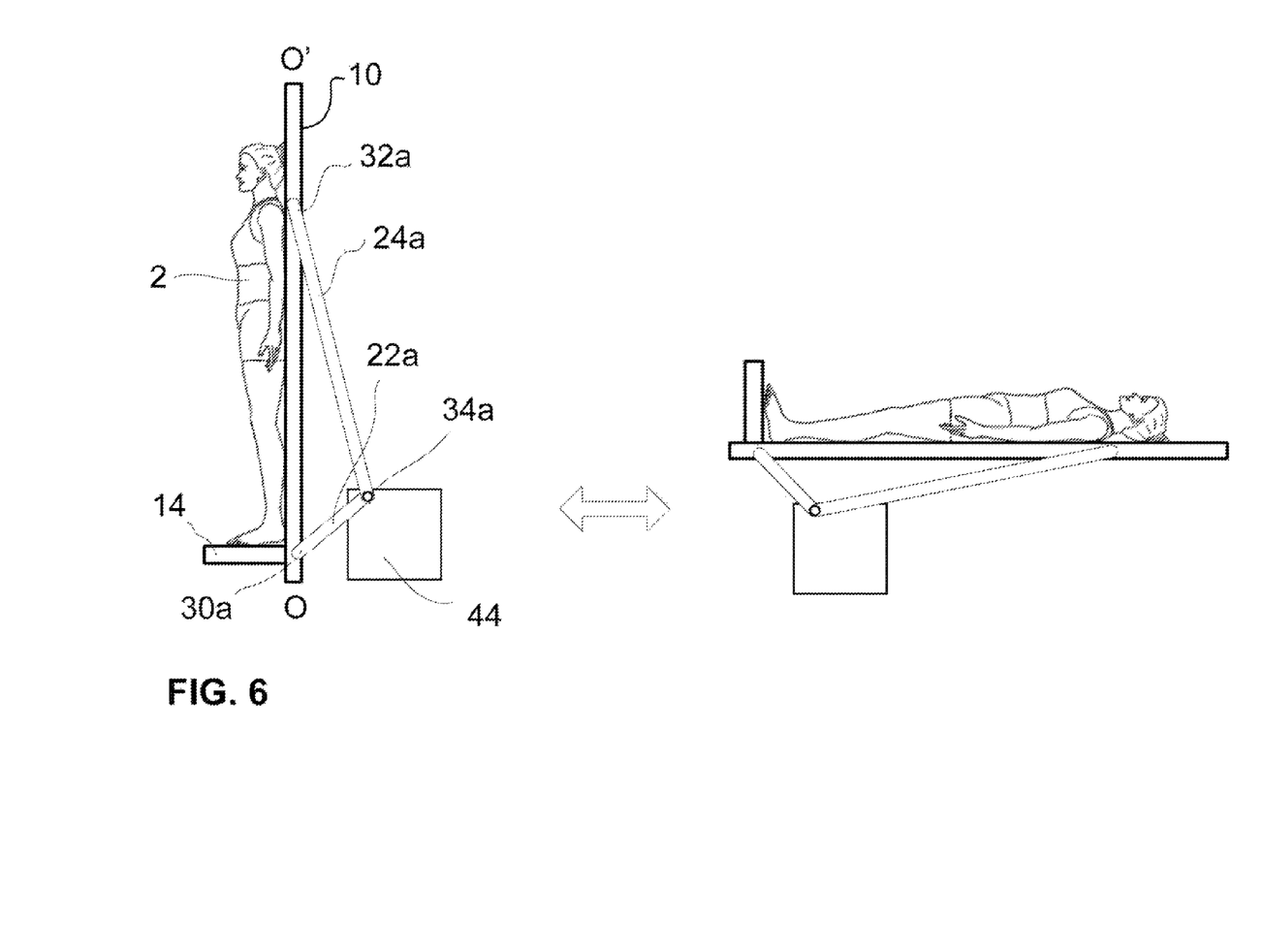
FIG. 6 is a schematic illustration of another embodiment in which the offset between the pivot joints 31 and 33 is zero.

For example, one particular modification reduces the offset between the pivot joints 31 and 33 to zero. This way, pivot points 31a and 33a are effectively merged into a single point (denoted as 34a in FIG. 6). In such an embodiment, the motion trajectory of the platform support 10 is fixed. Therefore, combining the two axles connecting joints 31a, 31b and 32a, 32b into a single axle 34 is a special case of the general scheme depicted in FIGS. 1-4.

Figure 7:
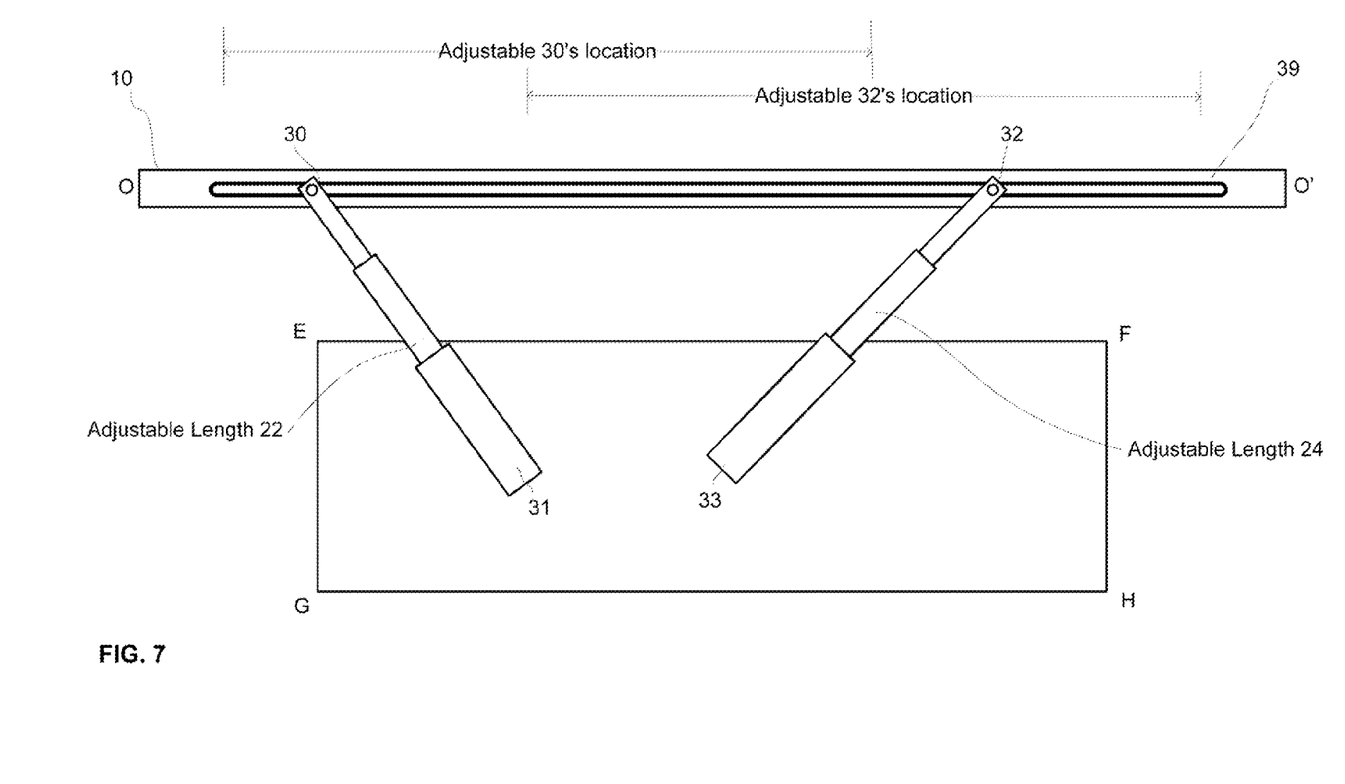
FIG. 7 is a schematic illustration of another embodiment in which the mechanical configuration of the system can be changed dynamically or by manual control.

FIG. 7 is a schematic illustration of another embodiment in which multiple mechanical parameters may be adjusted either dynamically (during use) or prior to each patient-loading operation. The arms 22, 24 are length-adjustable and attached the patient support platform 10 at movable joints 30, 32. The joints 30, 32 may comprise pins slidably inserted into tracks 39 running transversely along the patient support platform 10, or slidable/pivoting clamps affixed to rails, or the like. The arms 22, 24 are length-adjustable and may comprise, for example, pneumatic cylinders, telescoping segments, or other length-adjustable segments. The joints 31, 33 in the base cabinet 44 are likewise position-adjustable anywhere within an area defined by rectangle E-F-G-H, and may be adjusted and set in position statically or dynamically to achieve a reduced translational shift forward to the horizontal final position.

Specifically, all or any of the following mechanical parameters may be dynamically or statically adjusted:
  Joint positions (30,32) of the arms along the patient support platform OO';
  Joint positions (31,33) of the arms relative to the supporting base cabinet 44 within rectangle E-F-G-H;
  Lengths of the arms (22,24);

By adjusting any one or a combination of these parameters, a very broad range of starting position/orientation, ending position/orientation, and trajectories can be achieved.

One skilled in the art will readily understand that a variety of mechanisms may be provided for adjusting joint positions 31,33 of the arms 22, 24 relative to the supporting base cabinet 44 within rectangle E-F-G-H, and should be considered within the scope and spirit of the present invention. Nevertheless, one exemplary mechanism is herein disclosed.

Figure 8:
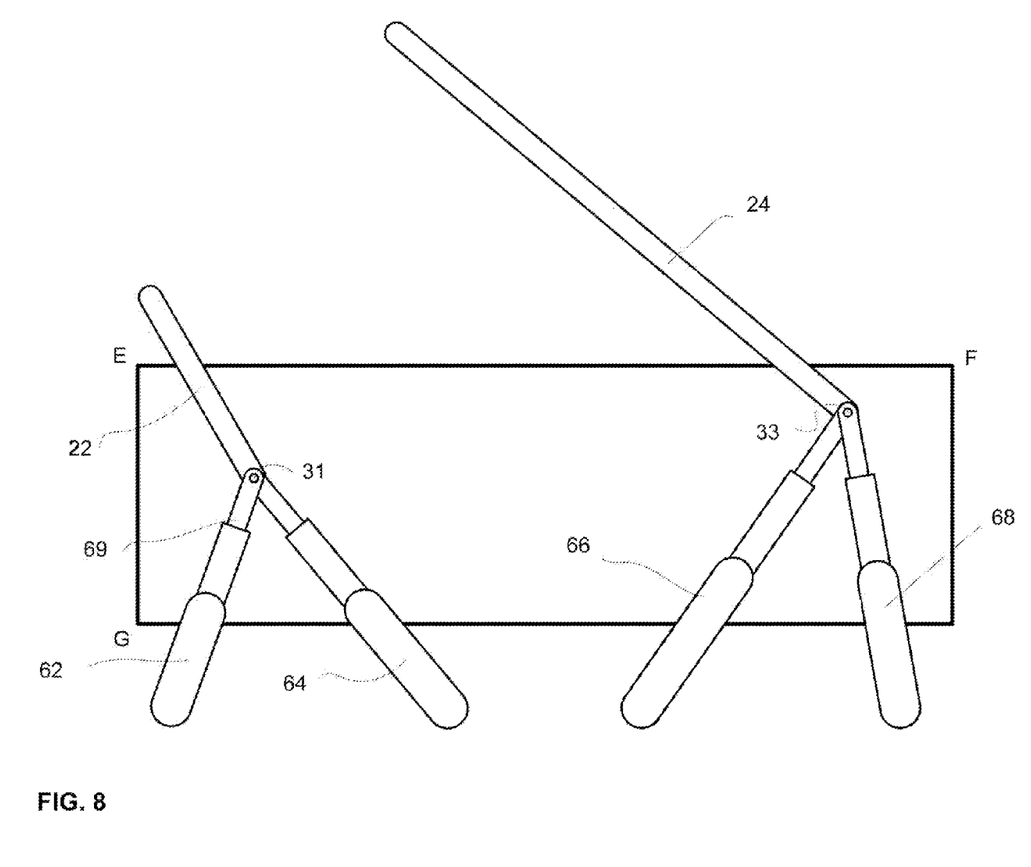
FIG. 8 is a schematic illustration showing how joint position 31 and 33 in FIG. 7 are dynamically moved.

FIG. 8 is a schematic illustration of one exemplary mechanism for adjusting joint positions 31,33 of the arms 22. 24 dynamically via mechanical or hydraulic mechanisms. Specifically, each arm 22, 24 is supported by a positioning mechanism comprising an opposed pair of length-adjustable struts 62, 64 and 66, 68, respectively. The length-adjustable struts 62-68 may be, for example, pneumatic cylinders, telescoping segments, or other length-adjustable segments. The length-adjustable struts 62, 64 and 66, 68 of each pair diverge from a common joint position 31,33 to a spaced-apart base, pivotally-affixed either to the supporting base cabinet 44 or some other understructure. The joint positions 31,33 can be adjusted anywhere within an area defined by rectangle E-F-G-H by relative extension/retraction of of the two length-adjustable struts 62, 64 and 66, 68 of each pair, which again allow individual adjustment of joint positions 31,33 either statically or dynamically to achieve a desired translational shift forward to the horizontal final position. With the mechanism of FIG. 8 it remains necessary to provide a driving motor to pivot at least one of the arms 22, 24 relative to the supporting base cabinet 44. Said driving motor cannot be fixed on either arm 20, 24 and still impart rotation. However, the driving motor can be fixed on any of the length-adjustable struts 62-68 and its actuator rotationally-engaged to the corresponding arm 22, 24. Thus, the driving motor(s) can be affixed, for example, to a motor bracket 69 which is in turn mounted to length-adjustable strut 62. It should now be apparent that the above-described embodiments provide a patient positioning method and device that is particularly suited for imaging and radiation treatments because it facilitates adjustment of both the spatial position and orientation of a patient in either a prone or supine position easily and accurately, so that a very broad range of starting position/orientation, ending position/orientation, and trajectories can be achieved.

The above-described embodiments and their alternative deployable uses is for the purpose of promoting an understanding of the principles of the invention. It should nevertheless be understood that no limitation of the scope of the invention is thereby intended, such alternations and further modifications in the illustrated device, and such further applications of the principles of the invention as illustrated herein being contemplated as would normally occur to one skilled in the art to which the invention relates.

What is claimed is:

1. A device for accurately positioning patients for medical imaging or treatment, comprising:
    a support platform including an elongate torso support section defined by four opposing corners bounding two opposing ends and opposing sides, and a foot support extending from one of the opposing ends of said torso support section at an angle;
    a fixed base;
    at least two supporting arms connecting said support platform to said base, one of said at least two supporting arms being attached to one of said two opposing ends of said support platform at a first passive pivot joint and extending at an angle therefrom to a first active pivot joint on said base, and the other of said at least two supporting arms being attached to another of said two opposing ends of said support platform at a second passive pivot joint and extending at an angle therefrom to a second active pivot joint on said base, said at least two supporting arms converging from said two opposing ends of said support platform to said base, all of said first active pivot joint, second active pivot joint, first passive pivot joint and second passive pivot joints having parallel axes of rotation; and
    a pair of actuators mounted in said base for transmitting a rotational force to said at least two supporting arms at said base, one of said pair of actuators driving said first active pivot joint and the other of said pair of actuators driving said second active pivot joint;
    whereby synchronous actuation of said at least two supporting arms in a common angular direction moves said supporting platform between a first spatial position and orientation and a second spatial position and orientation.

2. The patient positioning device according to claim 1, wherein said first spatial position and orientation comprises a vertical position on one side of said base and said second spatial position and orientation comprises a horizontal position on another side of said base.

3. The patient positioning device according to claim 2, wherein said foot support is vertically elevated in said second position.

4. The patient positioning device according to claim 1, wherein said at least two supporting arms comprises a pair of upper supporting arms and a pair of lower supporting arms.

5. The patient positioning device according to claim 4, wherein the support arms of each pair are the same length.

6. The patient positioning device according to claim 5, wherein the upper support arms are longer than the lower support arms.

7. The patient positioning device according to claim 1, wherein said support arms are journaled into the torso support section at sealed bearings.

8. The patient positioning device according to claim 1, wherein said support arms are attached to said base at a common pivot point.

9. The patient positioning device according to claim 5, wherein the pair of upper supporting arms and a pair of lower supporting arms are each attached to said base at a pivot joint, and the upper supporting arm pivot joints are connected by a first axle and said pair of lower supporting arm pivot joints are connected by a second axle.

10. The patient positioning device according to claim 5, wherein said first active pivot joint comprises a first axle and said second active pivot joint comprises a second axle, the pair of upper supporting arms both being attached from opposing corners at one end of said support platform to said first axle, and the pair of lower supporting arms both being attached from opposing corners at the opposing end of said support platform to said second axle.

11. The patient positioning device according to claim 1, wherein said at least two supporting arms consist of a pair of upper supporting arms and a pair of lower supporting arms.

12. The patient positioning device according to claim 1, wherein said at least two supporting arms consist of one upper supporting arm and one lower supporting arm.

13. The patient positioning device according to claim 1, wherein a length of said at least two supporting arms is calculated to establish a predetermined trajectory of said supporting platform while moving between said first spatial position and orientation and said second spatial position and orientation.

14. The patient positioning device according to claim 11, wherein a length of said at least two supporting arms may be selectively varied during actuation in said angular direction to dynamically change said predetermined trajectory while moving between said first spatial position and orientation and said second spatial position and orientation.

15. A device for accurately positioning patients for medical imaging or treatment, comprising:
    a support platform including an elongate rectangular torso support section defined by four opposing corners bounding two opposing ends and opposing sides, and a foot support extending from one of the opposing ends side of said torso support section at an angle;
    a base;
    a pair of upper supporting arms connecting said support platform to said base, said pair of upper supporting arms being attached to one of said two opposing ends of said support platform at passive pivot joints proximate two of said corners and extending at an angle therefrom, said pair of upper supporting arms being joined together by an axle at said base;
    a pair of lower supporting arms connecting said support platform to said base, said pair of upper supporting arms being attached to another of said two opposing ends of said support platform at passive pivot joints proximate two of said corners and extending at an angle therefrom, said pair of upper supporting arms being joined together by an axle at said base;
    said pair of lower supporting arms converging toward said pair of upper supporting arms about said base;

at least one actuator mounted in said base for transmitting a rotational force to at least one of said pair of upper supporting arms and said pair of lower supporting arms at said base;

whereby actuation of said at least one actuator moves said pair of upper supporting arms and said pair of lower supporting arms in a common angular direction and moves said supporting platform between a first spatial position and orientation and a second spatial position and orientation.

16. The patient positioning device according to claim 15, wherein said first spatial position and orientation comprises a vertical position on one side of said base and said second spatial position and orientation comprises a horizontal position on another side of said base.

17. The patient positioning device according to claim 16, wherein said foot support is vertically elevated in said second position.

18. The patient positioning device according to claim 15, wherein the pair of upper support arms are of equal length.

19. The patient positioning device according to claim 18, wherein the pair of lower support arms are of equal length.

20. The patient positioning device according to claim 19, wherein the pair of upper support arms are longer than the pair of lower support arms.

21. The patient positioning device according to claim 15, wherein said support arms are journaled into the torso support section at sealed bearings.

22. The patient positioning device according to claim 15, wherein a length of said at least two supporting arms is calculated to establish a predetermined trajectory of said supporting platform while moving between said first spatial position and orientation and said second spatial position and orientation.

23. The patient positioning device according to claim 22, wherein a length of said at least two supporting arms may be selectively varied during movement thereof in said angular direction to dynamically change said predetermined trajectory while moving between said first spatial position and orientation and said second spatial position and orientation.

24. A method for accurately positioning patients for medical imaging or treatment, comprising the steps of:
seating a patient on a support platform defined as an elongate rectangular torso support section with four opposing corners and two opposing sides, said support platform being coupled to a base by a pair of upper supporting arms and a pair of lower supporting arms;
articulating said patient via said support platform by activating a first actuator mounted in said base to transmit a rotational force to said pair of upper supporting arms at said base, and synchronously activating a second actuator mounted in said base to transmit a rotational force to said pair of lower supporting arms at said base;
moving said supporting platform between a first spatial position and orientation and a second spatial position and orientation.

25. A device for accurately positioning patients for medical imaging or treatment, comprising:
a support platform including an elongate torso support section with opposing sides;
a fixed base;
a pair of supporting arms connecting said support platform to said base, said pair of supporting arms being attached to said support platform at a corresponding pair of spaced pivot joints and extending at an angle therefrom, and said pair of supporting arms being attached to said base at a common pivot joint, all of said pivot joints having parallel axes of rotation;
the pair of upper supporting arms being connected by a first axle at said corresponding pivot joint and said pair of lower supporting arm pivot joints being connected by a second axle at said corresponding pivot;
and at least one actuator for transmitting a rotational force to at least one of said supporting arms; whereby actuation and transmission of said rotational force to said at least one supporting arm causes synchronous movement of said pair of supporting arms in a common angular direction and moves said supporting platform between a first spatial position and orientation and a second spatial position and orientation.

26. The patient positioning device according to claim 23, further comprising two pair of supporting arms including a pair of upper supporting arms and a pair of lower supporting arms.

27. The patient positioning device according to claim 24, wherein the pair of upper supporting arms and a pair of lower supporting arms are each attached to said base at a pivot joint, and the upper supporting arm pivot joints and lower supporting arm pivot joints are connected by an axle.

28. The patient positioning device according to claim 1, wherein the pair of spaced pivot joints at which said pair of supporting arms are attached may be selectively offset during actuation to dynamically change a trajectory between said first spatial position and orientation and said second spatial position and orientation.

29. The patient positioning device according to claim 25, wherein a length of said pair of supporting arms may be selectively changed during actuation to dynamically change a trajectory between said first spatial position and orientation and said second spatial position and orientation.

* * * * *